(12) United States Patent
Huber et al.

(10) Patent No.: US 7,084,312 B1
(45) Date of Patent: Aug. 1, 2006

(54) CATALYST AND METHOD FOR HYDROGENATING CARBONYL COMPOUNDS

(75) Inventors: Sylvia Huber, Zwingenberg (DE); Michael Jolyon Sprague, Mannheim (DE); Boris Breitscheidel, Limburgerhof (DE); Joachim Wulff-Döring, Frankenthal (DE); Michael Hesse, Worms (DE); Rolf Pinkos, Bad Dürkheim (DE); Shelue Liang, Ludwigshafen (DE); Otto Kumberger, Mannheim (DE); Marc Walter, Frankenthal (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 1316 days.

(21) Appl. No.: 10/070,275

(22) PCT Filed: Aug. 22, 2000

(86) PCT No.: PCT/EP00/08195

§ 371 (c)(1),
(2), (4) Date: Mar. 6, 2002

(87) PCT Pub. No.: WO01/17934

PCT Pub. Date: Mar. 15, 2001

(30) Foreign Application Priority Data

Sep. 8, 1999 (DE) ................................ 199 42 895

(51) Int. Cl.
*C07C 29/136* (2006.01)
*C07C 29/14* (2006.01)
*C07C 29/141* (2006.01)
*C07C 29/143* (2006.01)
*C07C 29/147* (2006.01)

(52) U.S. Cl. ........................ 568/881; 568/885; 568/862; 568/864; 568/861; 568/863; 568/876; 568/878; 568/880; 568/884; 568/814; 568/830; 568/903

(58) Field of Classification Search ................ 568/885, 568/862, 864, 861, 863, 876, 878, 880, 881, 568/884, 814, 830, 903
See application file for complete search history.

(56) References Cited

U.S. PATENT DOCUMENTS 3,923,694 A    12/1975   Cornwaithe ................. 252/463
5,334,779 A    8/1994    Kuo ........................... 568/864

FOREIGN PATENT DOCUMENTS

| DD | 256 515 | 5/1988 |
|----|---------|--------|
| DE | 195 05 347 | 9/1995 |
| DE | 198 09 418 | 9/1999 |
| EP | 0 217 513 | 4/1987 |
| EP | 0 296 734 | 12/1988 |
| EP | 0 523 818 | 1/1993 |
| FR | 2352588 | 11/1977 |
| GB | 1281112 | 7/1972 |

Primary Examiner—Elvis O. Price

(74) Attorney, Agent, or Firm—Novak Druce & Quigg, LLP; Jason D. Voight

(57) ABSTRACT

A process for the hydrogenation of an organic compound containing at least one carbonyl group comprises bringing the organic compound in the presence of hydrogen into contact with a shaped body which can be produced by a process in which
  (i) an oxidic material comprising copper oxide, zinc oxide and aluminum oxide is made available,
  (ii) pulverulent metallic copper or pulverulent cement or a mixture thereof is added to the oxidic material, and
  (iii) the mixture resulting from (ii) is shaped to form a shaped body.

7 Claims, No Drawings

US 7,084,312 B1

CATALYST AND METHOD FOR HYDROGENATING CARBONYL COMPOUNDS

This application is a 371 of PCT/EP00/08195, filed Aug. 22, 2000.

The present invention relates to a process for the hydrogenation of organic compounds containing at least one carbonyl group using a catalyst in whose production copper powder or cement is added. The present invention likewise relates to the catalyst itself and quite generally to the use of copper or cement powder in the production of catalysts having high selectivity combined with high stability.

The catalytic hydrogenation of carbonyl compounds such as carboxylic acids or carboxylic esters occupies an important position in the production lines of the basic chemicals industry.

In industrial processes, the catalytic hydrogenation of carbonyl compounds such as carboxylic esters is carried out virtually exclusively in fixed-bed reactors. Fixed-bed catalysts used are, apart from catalysts of the Raney type, especially support catalysts, for example copper, nickel or noble metal catalysts.

U.S. Pat. No. 3,923,694 describes, for example, a catalyst of the copper oxide/zinc oxide/aluminum oxide type. The disadvantage of this catalyst is that it has insufficient mechanical stability during the reaction and therefore disintegrates relatively quickly. This results in a drop in activity and the building-up of a differential pressure over the reactor due to the disintegrating catalyst bodies. As a consequence, the plant has to be shut down prematurely.

DE 198 09 418.3 describes a process for the catalytic hydrogenation of a carbonyl compound in the presence of a catalyst comprising a support, which comprises predominantly titanium dioxide and, as active component, copper or a mixture of copper with at least one metal selected from the group consisting of zinc, aluminum, cerium, noble metals and metals of transition group VIII, with the surface area of copper being not more than 10 $m^2/g$. Preferred support materials are mixtures of titanium dioxide with aluminum oxide or zirconium oxide or aluminum oxide and zirconium oxide. In a preferred embodiment, the catalyst material is shaped with addition of metallic copper powder.

DE-A 195 05 347 describes, quite generally, a process for producing catalyst pellets having a high mechanical strength, with a metal powder or a powder of a metal alloy being added to the material to be pelletized. Aluminum powder or copper powder, inter alia, is added as metal powder. However, in the case of a copper oxide/zinc oxide/aluminum oxide catalyst, the addition of aluminium powder gives a shaped body which has poorer lateral compressive strength than a shaped body produced without addition of aluminum powder, and, when used as catalyst, the shaped body of the invention displayed a poorer conversion activity than did catalysts produced without addition of aluminum powder. The document likewise discloses a hydrogenation catalyst comprising NiO, $ZrO_2$, $MoO_3$ and CuO, in which Cu powder, inter alia, was mixed during its production. However, this document gives no information on the selectivity or the activity.

DD 256 515 describes a process for preparing alcohols from synthesis gas using catalysts based on Cu/Al/Zn which are obtained by comilling and pelletization with metallic copper powder. The process described is mainly directed at the preparation of mixtures of $C_1$–$C_5$-alcohols, and the process is carried out in a reactor whose upper third contains a catalyst having a relatively high proportion of copper powder and whose lower third contains a catalyst having a lower proportion of copper powder.

It is an object of the present invention to overcome the disadvantages of the prior art and to provide processes for the catalytic hydrogenation of carbonyl compounds and to provide catalysts which have both a high mechanical stability and a high hydrogenation activity.

We have found that this object is achieved by mixing metallic copper powder or cement powder or a mixture thereof into a dried oxidic material made up of support material and active component and comprising copper oxide, zinc oxide and aluminum oxide and tableting the resulting mixture to give a shaped catalyst body which displays high activities and selectivities and has a high stability.

The present invention accordingly provides a process for the hydrogenation of an organic compound containing at least one carbonyl group, which comprises bringing the organic compound in the presence of hydrogen into contact with a shaped body which can be produced by a process in which (i) an oxidic material comprising copper oxide, zinc oxide and aluminum oxide is made available, (ii) pulverulent metallic copper or pulverulent cement or a mixture thereof is added to the oxidic material, and (iii) the mixture resulting from (ii) is shaped to form a shaped body.

In preferred embodiments, the shaped bodies of the present invention are used as uniform-composition catalysts, impregnated catalysts, coated catalysts and precipitated catalysts.

As support material in the catalyst of the present invention, preference is given to using a mixture of aluminum oxide, zinc oxide and possibly zinc-aluminum spinel. There are no particular restrictions regarding the preparation of the support material. In a preferred embodiment of the process of the present invention, an aqueous solution comprising zinc nitrate and aluminum nitrate is reacted with sodium carbonate and the resulting suspension is filtered and dried, and particularly preferably additionally calcined in a further step.

In the catalysts used in the process of the present invention, the active component copper and the active component zinc are applied to the support material used, without there being any restrictions in respect of the application method.

In particular, the following application methods are useful:

(A) Application of a copper salt solution and a zinc salt solution or a solution comprising copper and zinc salts to the prefabricated support in one or more impregnation steps. Subsequent to the impregnation, the support is dried and, if appropriate, calcined.

A1) The impregnation can be carried out by the "incipient wetness" method in which the support is moistened with an amount of impregnation solution corresponding to its water absorption capacity up to saturation. However, impregnation can also be carried out with excess solution.

A2) In the case of multistage impregnation methods, it is advantageous to carry out drying and, if appropriate, calcination between the individual impregnation steps. The multistage impregnation is particularly advantageous when the support is to be loaded with a relatively large amount of copper and/or a relatively large amount of zinc.

A3) In the impregnation, the inorganic support material is preferably used as a preshaped composition, for example as powder, spheres, extrudates or pellets. Particular preference is given to using it as powder.

B) Precipitation of a copper salt solution and a zinc salt solution or a solution comprising copper and zinc salts onto the prefabricated support. In a particularly preferred embodiment, this is present as powder in an aqueous suspension.

B1) In one embodiment (I), a copper salt solution and a zinc salt solution or a solution comprising copper and zinc salts is precipitated, preferably using sodium carbonate solution. An aqueous suspension of the support material is used as initial charge.

B2) In a further embodiment (II), the precipitated catalyst can be produced in a multistage process. Here, in a first stage, a powder is prepared as described in A3) and dried. This powder is converted into an aqueous suspension and used as initial charge for a procedure equivalent to that described in embodiment (I).

Precipitates resulting from A) or B) are filtered and preferably washed free of akali in a customary manner, as is described, for example, in DE 198 09 418.3.

Both the end products from A) and those from B) are dried at from 50 to 150° C., preferably at 120° C. and subsequently calcined if appropriate, preferably for 2 hours at generally from 200 to 600° C., in particular from 300 to 500° C.

As starting materials for A) and/or B), it is in principle known to use all Cu(I) and/or Cu(II) salts which are soluble in the solvents used for application to the support, for example nitrates, carbonates, acetates, oxalates or ammonium complexes and analogous zinc salts. For methods A) and B), particular preference is given to using copper nitrate.

In the process of the present invention, the above-described dried and possibly calcined powder is preferably converted into pellets, rings, annular pellets, extrudates, honeycombs or similar shaped bodies. All suitable methods known from the prior art are conceivable for this purpose.

The composition of the oxidic material is generally such that the proportion of copper oxide is in the range from 40 to 90% by weight, the proportion of zinc oxide is in the range from 10 to 50% by weight and the proportion of aluminum oxide is up to 50% by weight, in each case based on the total weight of the abovementioned oxidic constituents, with these three oxides together making up at least 80% by weight of the oxidic material after calcination and cement not being included as part of the oxidic material in the above sense.

In a preferred embodiment, the present invention accordingly provides a process as described in which the oxidic material comprises (a) copper oxide in a proportion in the range $60 \leq x \leq 80\%$ by weight, preferably $65 \leq x \leq 75\%$ by weight, (b) zinc oxide in a proportion in the range $15 \leq y \leq 35\%$ by weight, preferably $20 \leq y \leq 30\%$ by weight, and (c) aluminum oxide in a proportion in the range $2 \leq z \leq 20\%$ by weight, preferably $3 \leq z \leq 7\%$ by weight, in each case based on the total weight of the oxidic material after calcination, where $80 \leq x+y+z \leq 100$, in particular $95 \leq x+y+z \leq 100$, and cement is not included as part of the oxidic material in the above sense.

The process of the present invention and the catalysts of the present invention are distinguished by the addition of pulverulent copper or pulverulent cement or a mixture thereof as additive to the oxidic material prior to shaping.

In general, the amount of pulverulent copper or pulverulent cement or a mixture thereof added to the oxidic material is in the range from 1 to 40% by weight, preferably in the range from 2 to 20% by weight and particularly preferably in the range from 5 to 10% by weight, in each case based on the total weight of the oxidic material.

The present invention therefore also provides a process as described above in which the pulverulent metallic copper or the pulverulent cement or the mixture thereof is added in an amount in the range from 1 to 40% by weight, based on the total weight of the oxidic material.

The particle size of the copper powder or the cement powder is generally in the range from 0.1 to 1000 µm, preferably in the range from 0.5 to 500 µm and particularly preferably in the range from 1 to 300 µm.

In a preferred embodiment, use is made of copper powder and cement powder having a particle size distribution in which at least 45%, preferably at least 70%, particularly preferably at least 90%, of the copper or cement particles have particle sizes in the range from 10 to 100 µm.

The particle sizes are measured using a particle size measurement instrument model "HELOS 12KA/LA" from SYMPATEC. The SYMPATEC HELOS system employs the optical principle of laser light scattering for the rapid analysis of particle size distributions in suspensions, emulsions, aerosols and sprays. The HELOS measurement system comprises an optical arrangement in which laser, beam expander, measuring station, focussing lens and multielement photodetector are arranged in succession along the optical axis. The focussing lens positioned subsequently in the beam path positioned in the beam path collects the Fraunhofer scattering spectra produced by the particles and focusses them on the centrally arranged multielement photodetector. Depending on the particle size distribution, a radially symmetric intensity distribution whose energy density decreases with distance from the center and whose distribution is determined by the number and size of the particles in the measurement volume is formed. The intensity distribution is recorded by means of the multielement detector comprising 31 semicircular rings, converted into voltage-proportional values, stored in a subsequent data processor and taken over for further evaluation. From the measured intensities, the associated particle size distribution can be calculated by solution of a system of simultaneous linear equations.

The surface area of the copper powder or cement powder, determined by the BET method, is generally in the range from 0.01 to 20 m²/g, preferably in the range from 0.05 to 10 m²/g, particularly preferably in the range from 0.1 to 0.5 m²/g.

The present invention therefore also provides a process as described above in which the particle size of the pulverulent copper and the pulverulent cement is in the range from 0.1 to 1000 µm and the BET surface area is in the range from 0.01 to 2 m²/g.

As cement, preference is given to using an alumina cement. The alumina cement particularly preferably consists essentially of aluminum oxide and calcium oxide, in particular it comprises from about 75 to 85% by weight of aluminum oxide and from about 15 to 25% by weight of calcium oxide. It is also possible to use a cement based on magnesium oxide/aluminum oxide, calcium oxide/silicon oxide and calcium oxide/aluminum oxide/iron oxide.

In particular, the oxidic material may further comprise a proportion of not more than 10% by weight, preferably not more than 5% by weight, based on the total weight of the oxidic material, of at least one additional component selected from the group consisting of the elements Re, Fe, Ru, Co, Rh, Ir, Ni, Pd and Pt.

In a further preferred embodiment of the process of the invention, graphite is added in addition to the copper powder or the cement powder or the mixture thereof to the oxidic material prior to shaping to form the shaped body. Preference is given to adding such an amount of graphite that shaping to form a shaped body can be carried out more readily. In a preferred embodiment, from 0.5 to 5% by weight of graphite, based on the total weight of the oxidic material, is added. Here, it is immaterial whether the graphite is added to the oxidic material before or after or simultaneously with the copper powder or the cement powder or the mixture thereof.

The present invention accordingly also provides a process as described above in which graphite in an amount of from 0.5 to 5% by weight, based on the total weight of the oxidic material, is added to the oxidic material or the mixture resulting from (ii).

In a preferred embodiment, the present invention therefore also provides a shaped body comprising an oxidic material comprising
(a) copper oxide in a proportion in the range $60 \leq x \leq 80\%$ by weight, preferably $65 \leq x \leq 75\%$ by weight,
(b) zinc oxide in a proportion in the range $15 \leq y \leq 35\%$ by weight, preferably $20 \leq y \leq 30\%$ by weight, and
(c) aluminum oxide in a proportion in the range $2 \leq z \leq 20\%$ by weight, preferably $3 \leq z \leq 7\%$ by weight, in each case based on the total weight of the oxidic material after calcination, where $80 \leq x+y+z \leq 100$, in particular $95 \leq x+y+z \leq 100$,
metallic copper powder or cement powder or a mixture thereof in a proportion in the range from 1 to 40% by weight, based on the total weight of the oxidic material, and
graphite in a proportion of from 0.5 to 5% by weight, based on the total weight of the oxidic material,
where the sum of the proportions of oxidic material, metallic copper powder or cement powder or a mixture thereof and graphite makes up at least 95% by weight of the shaped body.

After addition of the copper powder or the cement powder or the mixture thereof and, if desired, graphite to the oxidic material, the shaped body obtained after shaping is, if desired, calcined at least once for a period of generally from 0.5 to 10 hours, preferably from 0.5 to 2 hours. The temperature in this calcination step or steps is generally in the range from 200 to 600° C., preferably in the range from 250 to 500° C. and particularly preferably in the range from 300 to 400° C.

In the case of shaping using cement powder, it may be advantageous to moisten the shaped body obtained before calcination with water and subsequently to dry it.

When the shaped body is used as catalyst in the oxidic form, it is prereduced by means of reducing gases, for example hydrogen, preferably hydrogen/inert gas mixtures, in particular hydrogen/nitrogen mixtures, at from 100 to 500° C., preferably from 150 to 350° C. and in particular from 180 to 200° C., prior to being brought into contact with the hydrogenation solution. This is preferably carried out using a mixture having a hydrogen content in the range from 1 to 100% by volume, particularly preferably in the range from 1 to 50% by volume.

In a preferred embodiment, the shaped body of the invention is activated in a manner known per se by treatment with reducing media prior to use as catalyst. The activation is carried out either beforehand in a reduction oven or after installation in the reactor. If the catalyst has been activated beforehand in the reduction oven, it is installed in the reactor and supplied directly with the hydrogenation solution under hydrogen pressure.

A preferred area of application of the shaped bodies produced by the process of the present invention is the hydrogenation of organic compounds containing carbonyl groups in a fixed bed. However, other embodiments such as a fluidized-bed reaction using catalyst material in upward and downward swirling motion are likewise possible. The hydrogenation can be carried out in the gas phase or in the liquid phase. The hydrogenation is preferably carried out in the liquid phase, for example in the downflow mode or upflow mode.

When the hydrogenation is carried out in the downflow mode, the liquid starting material comprising the carbonyl compound to be hydrogenated is allowed to trickle over the catalyst bed in the reactor which is under hydrogen pressure, forming a thin liquid film on the catalyst. On the other hand, when the hydrogenation is carried out in upflow mode, hydrogen is introduced into the reactor flooded with the liquid reaction mixture and the hydrogen passes through the catalyst as rising gas bubbles.

In one embodiment, the solution to be hydrogenated is pumped over the catalyst bed in a single pass. In another embodiment of the process of the present invention, part of the product is continuously taken off as product stream after passing through the reactor and, if desired, is passed through a second reactor as defined above. The other part of the product is combined with fresh starting material comprising the carbonyl compound and fed back into the reactor. This mode of operation will hereinafter be referred to as the circulation mode.

If the downflow mode is chosen as embodiment of the present invention, the circulation mode is preferred. Further preference is given to carrying out the hydrogenation in the circulation mode using a main reactor and an after-reactor.

The process of the present invention is suitable for the hydrogenation of carbonyl compounds such as aldehydes and ketones, carboxylic acids, carboxylic esters or carboxylic anhydrides to give the corresponding alcohols, with preference being given to aliphatic and cycloaliphatic, saturated and unsaturated carbonyl compounds. In the case of aromatic carbonyl compounds, formation of undesirable by-products by hydrogenation of the aromatic ring may occur. The carbonyl compounds may bear further functional groups such as hydroxyl or amino groups. Unsaturated carbonyl compounds are generally hydrogenated to the corresponding saturated alcohols. The term "carbonyl compounds" used in the context of the invention encompasses all compounds containing a C=O group, including carboxylic acids and their derivatives. Of course, it is also possible to hydrogenate mixtures of two or more carbonyl compounds. Furthermore, each individual carbonyl compound to be hydrogenated can also contain more than one carbonyl group.

The process of the present invention is preferably used for the hydrogenation of aliphatic aldehydes, hydroxyaldehydes, ketones, acids, esters, anhydrides, lactones and sugars.

Preferred aliphatic aldehydes are branched and unbranched, saturated and/or unsaturated aliphatic $C_2$–$C_{30}$-aldehydes, which are obtainable, for example, by means of the oxo process from linear or branched olefins having internal or terminal double bonds. It is also possible to hydrogenate oligomeric compounds containing more than 30 carbonyl groups.

Examples of aliphatic aldehydes are:

Formaldehyde, propionaldehyde, n-butyraldehyde, isobutyraldehyde, valeraldehyde, 2-methylbutyraldehyde, 3-methylbutyraldehyde (isovaleraldehyde), 2,2-dimethylpropionaldehyde (pivalaldehyde), caproaldehyde, 2-methylvaleraldehyde, 3-methylvaleraldehyde, 4-methylvaleraldehyde, 2-ethylbutyraldehyde, 2,2-dimethylbutyraldehyde, 3,3-dimethylbutyraldehyde, caprylic aldehyde, capric aldehyde, glutaraldehyde.

Apart from the short-chain aldehydes mentioned, long-chain aliphtic aldehydes as can be obtained, for example, by means of the oxo process from linear α-olefins, are also particularly suitable.

Particular preference is given to enalization products such as 2-ethylhexenal, 2-methylpentenal, 2,4-diethyloctenal or 2,4-dimethylheptenal.

Preferred hydroxyaldehydes are $C_3$–$C_{12}$-hydroxyaldehydes as are obtainable, for example, from aliphatic and cycloaliphatic aldehydes and ketones by aldol reaction with themselves or formaldehyde. Examples are 3-hydroxypropanal, dimethylolethanal, trimethylol-ethanal (pentaerythrital), 3-hydroxybutanal (acetaldol), 3-hydroxy-2-ethylhexanal (butyl aldol), 3-hydroxy-2-methylpentanal (propene aldol), 2-methylolpropanal, 2,2-dimethylolpropanal, 3-hydroxy-2-methylbutanal, 3-hydroxypentanal, 2-methylolbutanal, 2,2-dimethylolbutanal, hydroxypivalaldehyde. Particular preference is given to hydroxypivalaldehyde (HPA) and dimethylolbutanal (DMB).

Preferred ketones are acetone, butanone, 2-pentanone, 3-pentanone, 2-hexanone, 3-hexanone, cyclohexanone, isophorone, methyl isobutyl ketone, mesityl oxide, acetophenone, propiophenone, benzophenone, benzal-acetone, dibenzalacetone, benzalacetophenone, 2,3-butanedione, 2,4-pentanedione, 2,5-hexanedione and methyl vinyl ketone.

Furthermore, carboxylic acids and derivatives thereof, preferably those having 1–20 carbon atoms, can be reacted. In particular, the following may be mentioned:

carboxylic acids such as formic acid, acetic acid, propionic acid, butyric acid, isobutyric acid, n-valeric acid, trimethylacetic acid ("pivalic acid"), caproic acid, enanthic acid, caprylic acid, capric acid, lauric acid, myristic acid, palmitic acid, stearic acid, acrylic acid, methacrylic acid, oleic acid, elaidic acid, linoleic acid, linolenic acid, cyclohexanecarboxylic acid, benzoic acid, phenylacetic acid, o-toluic acid, m-toluic acid, p-toluic acid, o-chlorobenzoic acid, p-chlorobenzoic acid, o-nitrobenzoic acid, p-nitrobenzoic acid, salicylic acid, p-hydroxybenzoic acid, anthranilic acid, p-aminobenzoic acid, oxalic acid, malonic acid, succinic acid, glutaric acid, adipic acid, pimelic acid, suberic acid, azelaic acid, sebacic acid, maleic acid, fumaric acid, phthalic acid, isophthalic acid, terephthalic acid;

carboxylic esters such as the $C_1$–$C_{10}$-alkyl esters of the abovementioned carboxylic acids, in particular methyl formate, ethyl acetate, butyl butyrate, dialkyl esters of phthalic acid, isophthalic acid, terephthalic acid, adipic acid and maleic acid, e.g. the dimethyl esters of these acids, methyl (meth)acrylate, butyrolactone, caprolactone and polycarboxylic esters, e.g. polyacrylic and polymethacrylic esters and their copolymers, and polyesters, e.g. polymethyl methacrylate or terephthalic esters, and other industrial plastics; in these cases, the reactions carried out are, in particular, hydrogenolyses, i.e. the reaction of esters to form the corresponding acids and alcohols;

fats;

carboxylic anhydrides such as the anhydrides of the abovementioned carboxylic acids, in particular acetic anhydride, propionic anhydride, benzoic anhydride and maleic anhydride;

carboxamides such as formamide, acetamide, propionamide, stearamide, terephthalamide.

It is also possible for hydroxycarboxylic acids, e.g. lactic, malic, tartaric or citric acid, or amino acids, e.g. glycine, alanine, proline and arginine, and peptides to be reacted.

As particularly preferred organic compounds, saturated or unsaturated carboxylic acids, carboxylic esters, carboxylic anhydrides or lactones or mixtures of two or more thereof are hydrogenated.

The present invention therefore also provides a process as described above in which the organic compound is a carboxylic acid, a carboxylic ester, a carboxylic anhydride or a lactone.

Examples of these compounds are, inter alia, maleic acid, maleic anhydride, succinic acid, succinic anhydride, adipic acid, 6-hydroxycaproic acid, 2-cyclododecylpropionic acid, the esters of the abovementioned acids, for example the methyl, ethyl, propyl or butyl ester. Further examples are γ-butyrolactone and caprolactone.

In a very particularly preferred embodiment, the present invention provides a process as described above in which the organic compound is adipic acid or an ester of adipic acid.

The carbonyl compound to be hydrogenated can be fed to the hydrogenation reactor either alone or as a mixture with the product of the hydrogenation reaction, and can be fed in in undiluted form or using an additional solvent. Suitable additional solvents are, in particular, water and alcohols such as methanol, ethanol and the alcohol formed under the reaction conditions. Preferred solvents are water, THF and NMP; particular preference is given to water.

The hydrogenation both in the upflow mode and in the downflow mode, in each case preferably in the circulation mode, is generally carried out at from 50 to 350° C., preferably from 70 to 300° C., particularly preferably from 100 to 270° C., and a pressure in the range from 3 to 350 bar, preferably in the range from 5 to 330 bar, particularly preferably in the range from 10 to 300 bar.

In a very particularly preferred embodiment, the catalysts of the present invention are used in processes for preparing hexanediol and/or caprolactone, as are described in DE 196 07 954, DE 196 07 955, DE 196 47 348 and DE 196 47 349.

High conversions and selectivities are achieved in the process of the present invention using the catalysts of the present invention. At the same time, the catalysts of the present invention have a high chemical and mechanical stability. The advantageous abrasion behavior, which is reflected in low abrasion values, is of particular importance here.

The present invention therefore provides quite generally for the use of pulverulent metallic copper or pulverulent cement or a mixture thereof as additive in the production of a catalyst for increasing both the mechanical stability and the activity and selectivity of the catalyst.

In a preferred embodiment, the present invention provides for the use as described above of such a catalyst comprising copper as active component.

The mechanical stability of solid-state catalysts and specifically the catalysts of the present invention is described by the parameters abrasion and lateral compressive strength.

The lateral compressive strength was determined for the purposes of the present patent application by means of a "Z 2.5/T 919" instrument of Zwick (Ulm), and the abrasion was determined in accordance with ASTM Designation D 4058-81. In the case of both the reduced catalysts and the used catalysts, the measurement were carried out under a nitrogen atmosphere so as to avoid reoxidation of the catalysts.

The following examples illustrate the invention.

EXAMPLES

Example 1

Production of Catalyst 1

Production of the Support 450 g of $Al(NO_3)_3 \cdot 9H_2O$ were added to 649 g of a well-stirred aqueous solution of zinc nitrate having a zinc content of 14.5% by weight and the mixture was made up to a volume of 1.25 l with water in order to dissolve the aluminum salt (solution A). In a separate vessel, 474 g of anhydrous sodium carbonate were dissolved in water and the solution was made up to 2 l with water (solution B).

Solution A and solution B were heated to 50° C. and fed via separate lines into a precipitation vessel containing a well-stirred solution of 20 g of $NaHCO_3$ in 350 ml of water which had been heated to 50° C. The pH was brought to 6.8 over a period of about 3 minutes by appropriate adjustment of the feed rates of the solutions A and B. While keeping the pH constant at 6.8 and maintaining the temperature at 50° C., all of solution A was reacted with sodium carbonate. The suspension formed in this way was subsequently stirred for 3 hours, with the pH being maintained at 6.8 by occasional addition of dilute nitric acid. The suspension was filtered and washed with distilled water until the nitrate content of the washings was <10 ppm. The filter cake was dried at 120° C. for 16 hours and subsequently calcined at 425° C. for 1 hour.

Production of the Catalyst

A mixture of 432 g of a nitric acid solution of copper nitrate having a copper content of 15.5% by weight and 95 g of a nitric acid solution of zinc nitrate having a zinc content of 14.5% by weight was diluted with water to a volume of 500 ml and heated to 70° C. While stirring, 25.1 g of the above-described pulverulent calcined support was slowly added over a period of about 5 minutes and the resulting milky suspension was stirred for 15 minutes (suspension C).

In a separate vessel, 474 g of anhydrous sodium carbonate were dissolved in water and the solution was made up to 2 l with water and heated to 70° C. (solution D). Suspension C and solution D were fed via separate lines into a precipitation vessel which was provided with a stirrer and contained 350 ml of water heated to 70° C. The pH was brought to 7.4 by appropriate adjustment of the feed rates of the suspension C and solution D.

While keeping the pH constant at 7.4 and maintaining a temperature of 70° C., all of suspension C was reacted with sodium carbonate. The suspension formed in this way was subsequently stirred for another 2 hours, with the pH being maintained at 7.4 by occasional addition of dilute nitric acid or sodium carbonate solution D. The suspension was filtered and washed with distilled water until the nitrate content of the washings was <10 ppm.

The filter cake was dried at 120° C. for 16 hours and subsequently calcined at 430° C. for 1 hour. The brownish black catalyst powder obtained in this way was mixed with 1.5% by weight of graphite and 5% by weight of copper powder (grade FFL No. 10914 from Norddeutsche Affinerie, having a BET surface area of 0.23 $m^2/g$ and a particle size distribution in which 92% of the particles lie in a size range from 10 to 100 μm) and pressed to form pellets having a diameter of 3 mm and a height of 3 mm. The pellets were finally calcined at 330° C. for 1 hour.

The catalyst produced in this way has the chemical composition 66% CuO/24% ZnO/5% $Al_2O_3$/5% Cu. The lateral compressive strength and the abrasion in the oxidic and reduced states are shown in Table 1.

Example 2

Hydrogenation of Dimethyl Adipate Over Catalyst 1

Dimethyl adipate was hydrogenated continuously in the downflow mode with recirculation (feed/recycle ratio=10/1) at a WHSV of 0.5 kg/(1*h), a pressure of 240 bar and reaction temperatures of 200° C. and 220° C. in a vertical tube reactor charged with 200 ml of catalyst 1. The experiment was carried out for a total time of 14 days. GC analysis found ester conversions of 99% and 100%, hexanediol contents of 57% and 62% and methanol contents of 30% and 31% in the reaction product at 200° C. and 220° C., respectively. After removal from the reactor, the catalyst was found to be still completely intact and had a high mechanical stability. Lateral compressive strength and abrasion are shown in Table 1. The experimental results are summarized once more in Table 2.

Example 3

Production of Catalyst 2

Catalyst 2 was produced using a method analogous to that for catalyst 1 in Example 1, but 10% of copper powder of the grade Unicoat 2845 from Schlenck having a BET surface area of 2.34 $m^2/g$ and a particle size distribution in which 77% of the particles lie in the size range from 10 to 100 μm was added and the pellets were calcined at 400° C.

The catalyst produced in this way has the chemical composition 63% CuO/22% ZnO/5% $Al_2O_3$/10% Cu. The lateral compressive strength and the abrasion in the oxidic and reduced states are shown in Table 1.

Example 4

Hydrogenation of Dimethyl Adipate Over Catalyst 2

Dimethyl adipate was hydrogenated continuously in the downflow mode with recirculation (feed/recycle ratio=10/1) at a WHSV of 0.5 kg/(1*h), a pressure of 240 bar and reaction temperatures of 200° C. and 220° C. in a vertical tube reactor charged with 200 ml of catalyst 2. The experiment was carried out for a total time of 14 days. GC analysis found ester conversions of 98% in each case, hexanediol contents of 55% and 59% and methanol contents of 26% and 28% in the reaction product at 200° C. and 220° C., respectively. After removal from the reactor, the catalyst was found to be still completely intact and had a high mechanical stability. Lateral compressive strength and abrasion are shown in Table 1. The experimental results are summarized once more in Table 2.

Example 5

Catalyst 3 was produced using a method analogous to that for catalyst 2 in Example 3, but 5% of Secar cement grade 80 from Lafarge having a BET surface area of 7.5 $m^2/g$ and a particle size distribution in which 49% of the particles lie in the size range from 10 to 100 μm was added. The pellets were moistened for 6 hours, dried in air and subsequently calcined at 400° C. for 2 hours.

The catalyst produced in this way has the chemical composition 66% CuO/24% ZnO/5% $Al_2O_3$/5% cement. The lateral compressive strength and the abrasion in the oxidic and reduced states are shown in Table 1.

Example 6

Hydrogenation of Dimethyl Adipate Over Catalyst 3

Dimethyl adipate was hydrogenated continuously in the downflow mode with recirculation (feed/recycle ratio=10/1) at a WHSV of 0.5 kg/(1*h), a pressure of 240 bar and reaction temperatures of 200° C. and 220° C. in a vertical tube reactor charged with 200 ml of catalyst 3. The experiment was carried out for a total time of 14 days. GC analysis found ester conversions of 94% and 97%, hexanediol contents of 50% and 57% and methanol contents of 26% and 28% in the reaction product at 200° C. and 220° C., respectively. After removal from the reactor, the catalyst was found to be still completely intact and had a high mechanical stability. Lateral compressive strength and abrasion are shown in Table 1. The experimental results are summarized once more in Table 2.

Example 7

Production of a Comparative Catalyst

The catalyst was produced exactly as described in Example 1 of U.S. Pat. No. 3,923,694. The catalyst produced in this way had the chemical composition 70% CuO/25% ZnO/5% $Al_2O_3$. The lateral compressive strength and the abrasion in the oxidic and reduced states are shown in Table 1.

Example 8

Hydrogenation of Dimethyl Adipate Over the Comparative Catalyst

Dimethyl adipate was hydrogenated continuously in the downflow mode with recirculation (feed/recycle ratio=10/1) at a WHSV of 0.5 kg/(1*h), a pressure of 240 bar and reaction temperatures of 200° C. and 220° C. in a vertical tube reactor charged with 200 ml of the comparative catalyst. The experiment was carried out for a total time of 14 days. GC analysis found ester conversions of 92% and 96%, hexanediol contents of 48% and 58% and methanol contents of 25% and 28% in the reaction product at 200° C. and 220° C., respectively. After removal from the reactor, the catalyst was still completely intact but the mechanical stability had been reduced considerably. Lateral compressive strength and abrasion are shown in Table 1. The experimental results are summarized in Table 2.

TABLE 1

| Catalyst | Lateral compressive strength (oxidic)/kg | Abrasion (oxidic)/ % by weight | Lateral compressive strength (reduced)/kg | Abrasion reduced)/ % by weight | Lateral compressive strength (after removal from the reactor)/kg | Abrasion (after removal from the reactor)/ % by weight |
|---|---|---|---|---|---|---|
| Catalyst 1 | 5.5 | 3.2 | 3.9 | 1.2 | 4.3 | 1.8 |
| Catalyst 2 | 18.2 | 1.5 | 6.7 | 2.0 | 2.0 | 3.9 |
| Catalyst 3 | 6.3 | 2.3 | 3.9 | 3.5 | 4.0 | 1.2 |
| Comparative catalyst | 12.1 | 0.4 | 4.8 | 12.3 | 3.8 | 94.5 |

The data in Table 1 show that the novel catalysts 1 to 3 display a significantly higher mechanical stability, in particular significantly lower abrasion values, than the comparative catalyst both in the reduced state and after removal from the reactor.

The data in Table 2 below show that the catalysts of the present invention have considerably higher hydrogenation activities, i.e. higher conversions of dimethyl adipate, at 200° C. and 220° C. than the comparative catalyst, and also tend to give higher selectivities to the desired product, i.e. higher contents of the target products hexanediol and methanol in the output from the reactor.

TABLE 2

| Catalyst | Reaction temperature/° C. | Conversion of dimethyl adipate/% | Hexanediol content in the reaction product/% | Methanol content in the reaction product/% |
|---|---|---|---|---|
| Catalyst 1 | 200 | 99 | 57 | 30 |
|  | 220 | 100 | 62 | 31 |
| Catalyst 2 | 200 | 98 | 55 | 26 |
|  | 220 | 98 | 59 | 28 |
| Catalyst 3 | 200 | 94 | 50 | 26 |
|  | 220 | 97 | 57 | 28 |
| Comparative catalyst | 200 | 92 | 48 | 25 |
|  | 220 | 96 | 58 | 28 |

What is claimed is:

1. A process for the hydrogenation of an organic compound containing at least one carbonyl group, which comprises bringing the organic compound in the presence of hydrogen into contact with a shaped body which is produced by a process in which
   (i) an oxidic material comprising copper oxide, zinc oxide and aluminum oxide is made available,
   (ii) pulverulent metallic copper or pulverulent cement or a mixture thereof is added to the oxidic material, and
   (iii) the mixture resulting from (ii) is shaped to form a shaped body.

2. A process as claimed in claim 1, wherein the oxidic material comprises
   (a) copper oxide in a proportion x in the range from 60 to 80% by weight,
   (b) zinc oxide in a proportion y in the range from 15 to 35% by weight, and
   (c) aluminum oxide in a proportion z in the range from 2 to 20% by weight, in each case based on the total weight of the oxidic material after calcination, where x+y+z is in the range from 80 to 100% by weight, and cement is not included as part of the oxidic material in the above sense.

3. A process as claimed in claim 1, wherein the pulverulent metallic copper or the pulverulent cement or the mixture thereof is added in an amount in the range from 1 to 40% by weight, based on the total weight of the oxidic material.

4. A process as claimed in claim 1 wherein the particle size of the pulverulent copper and of the pulverulent cement is in the range from 0.1 to 100 μm.

5. A process as claimed in claim 1, wherein graphite is added in an amount in the range from 0.5 to 5% by weight, based on the total weight of oxidic material, to the oxidic material or the mixture resulting from (II).

6. A process as claimed in claim 1, wherein the organic compound is a carboxylic acid, a carboxylic ester, a carboxylic anhydride or a lactone.

7. A process as claimed in claim 6, wherein the organic compound is adipic acid or an ester of adipic acid.

* * * * *

UNITED STATES PATENT AND TRADEMARK OFFICE
CERTIFICATE OF CORRECTION

PATENT NO.         : 7,084,312 B1                                          Page 1 of 1
APPLICATION NO.    : 10/070275
DATED              : August 1, 2006
INVENTOR(S)        : Huber et al.

It is certified that error appears in the above-identified patent and that said Letters Patent is hereby corrected as shown below:

Claim 4, col. 14, indicated line 10: "0.1 to 100 μm" should read --0.1 to 1000 μm--

Claim 5, col. 14, indicated line 14: "from (II)" should read --from (ii)--

Signed and Sealed this

Seventeenth Day of April, 2007

JON W. DUDAS
*Director of the United States Patent and Trademark Office*